US00PP15975P3

(12) United States Plant Patent
Schräder

(10) Patent No.: US PP15,975 P3
(45) Date of Patent: Sep. 20, 2005

(54) **VARIETY OF *OSTEOSPERMUM* PLANT NAMED 'SUMOST 02'**

(50) Latin Name: *Osteospermum ecklonis*
Varietal Denomination: Sumost 02

(75) Inventor: Ralf Schräder, Lüdinghausen (DE)

(73) Assignee: Ralf Shrader, Ludinghausen (DE)

( * ) Notice: Subject to any disclaimer, the term of this patent is extended or adjusted under 35 U.S.C. 154(b) by 31 days.

(21) Appl. No.: 10/456,672

(22) Filed: Jun. 6, 2003

(65) Prior Publication Data

US 2004/0250328 P1 Dec. 9, 2004

(51) Int. Cl.[7] ..... A01H 5/00

(52) U.S. Cl. ..... Plt./360

(58) Field of Search ..... Plt./360

(56) References Cited

PUBLICATIONS

UPOV–ROM GTITM Computer Database Feb. 2004, GTI Jouve Retrieval Software, Citation for 'Sumost 02'.*

* cited by examiner

*Primary Examiner*—Anne Marie Grunberg
*Assistant Examiner*—Annette H Para
(74) *Attorney, Agent, or Firm*—The Webb Law Firm

(57) ABSTRACT

A new and distinct *Osteospermum* plant that exhibits orange flowers and reddish-purple disc florets.

2 Drawing Sheets

Botanical classification: *Osteospermum ecklonis.*
Varietal denomination: 'Sumost 02'.

BACKGROUND OF THE INVENTION

The present invention comprises a new and distinct cultivar of *Osteospermum* plant known by the varietal name 'Sumost 02'. The new variety was discovered in June 2001 in a selected breeding program in Lüdinghausen, Germany designed to produce a new variety of orange *Osteospermum* that is upright and exhibits strong root disease resistance. The new variety was selected from a cross of proprietary unpatented breeding plants, Seedling 2759 (female parent) and Seedling 115/2 (male parent). The new variety exhibits similar summer blooming to its parents, but is orange in color and has a semi-erect habit. The new variety flowers during the summer similar to 'Seikimora' (U.S. Plant Pat. No. 13,409), but 'Sumost 02' has larger flowers, a stronger branching habit, a semi-erect habit during the flowering period and a lighter flower color. The new variety was first asexually reproduced in June 2001 by cuttings in L üdinghausen, Germany. The new variety has been trial and field tested in Lüdinghausen and has been found to retain its distinctive characteristics and remain true to type through successive propagations.

The following traits distinguish 'Sumost 02' as a new and distinct cultivar:

1. 'Sumost 02' flowers during the summer;
2. 'Sumost 02' flowers without a cool period;
3. 'Sumost 02' has many ray florets;
4. No white band is present on the apex of the ray floret;
5. The upper and lower surface flower color is 29A Orange with a partial 165C Greyed-orange lower surface; and
6. The color of the disc floret is 59A Red-purple; and
7. The branching habit is at first upright and then semi-erect in the summer.

DESCRIPTION OF THE DRAWINGS

The accompanying photographic drawings illustrate the new variety, with the color being as nearly true as is possible with color illustrations of this type.

DESCRIPTION OF THE PLANT

Figure 1:
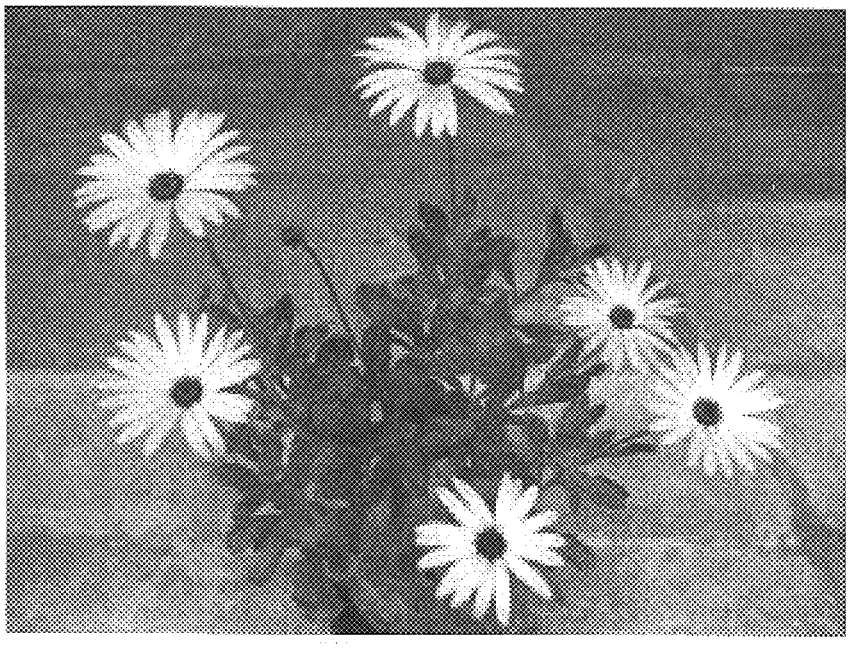
FIG. 1 is a photograph of the plant.
Figure 2:
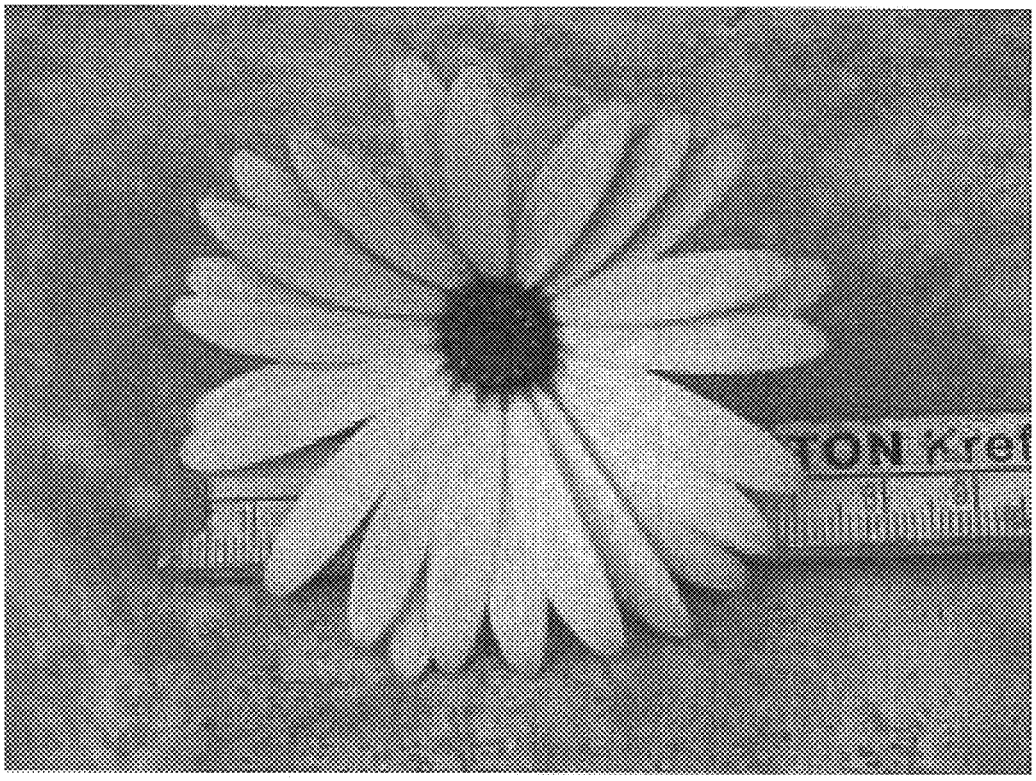
FIG. 2 is a close up view of the blooms of the new plant.

The following detailed description sets forth characteristics of the new cultivar. The data which defines these characteristics were collected by asexual reproductions by cuttings carried out in Lüdinghausen Germany. Flowering plants were grown in 12 cm containers at temperatures between 14° C. to 16° C. and in a sunny place. Color measurements were taken indoors under artificial light. The new variety was four months old when described. Color references are primarily to the 2001 R.H.S. Colour Chart of The Royal Horticultural Society of London.

PLANT

Time to initiate roots: About 4 days at 17° C.
Time to develop roots: About 8 days at 17° C.
Time to produce a finished flowering plant from a rooted cutting: About 12 weeks in a 12 cm container.
Form: Spreading.
Height: Approximately 30–35 cm.
Diameter: Approximately 25 cm.
Vigor: Good before flowering.
Branching habit: Upright; semi-erect at the end of summer.
Lateral branches:
*Length.*—Primary: 30–35 cm. Secondary: 20–25 cm.
*Diameter.*—Primary: 8 mm. Secondary: 5 mm.
*Internode length.*—2.5 cm.
*Strength.*—Medium.
*Shape.*—Pentagonal.
*Pubescence.*—Smooth.
*Color.*—145A.

Foliage:
*Arrangement.*—Alternate.
*Leaf length.*—5.0–6.0 cm.
*Leaf width.*—2.5 cm.
*Overall shape.*—Obovate.
*Aspect.*—Weak.
*Apex.*—Obtuse.
*Base.*—Obtuse.
*Margin.*—Entire; with some large serration.
*Pubescence.*—None.
*Color.*—Young leaves: Upper surface: 139A. Lower surface: 138A. Mature leaves: Upper surface: 138A. Lower surface: 138B.
*Petiole.*—No petiole present; the leaf is directly connected to the stamen.
*Veins.*—Color: Upper surface: 145C. Lower surface: 145C.

FLOWER

Natural flowering season: March to October.
Form: Actinomorphic.
Inflorescence position: Top.
Arrangement: Ray floret overlaps the disc floret.
Number of flowers per plant: Approximately 30.
Size:
*Diameter.*—7.5–8.0 cm.
*Height.*—1.5 cm.
*Disc diameter.*—1.2 cm.
Ray florets:
*Length.*—3.8–4.0 cm.
*Width.*—0.7–0.8 cm.
*Shape.*—Long; obovate.
*Apex.*—Obtuse.
*Base.*—Acute.
*Margin.*—Entire.
*Aspect.*—Weak.
*Texture.*—Smooth.
*Number per inflorescence.*—26.
*Color.*—When opening and fully opened: Upper surface: 29A. Lower surface: 29A with partial 165C.
Disc florets:
*Length.*—5 mm.
*Width.*—1 mm.
*Shape.*—Tube shaped.
*Number of lobes.*—2.
*Number per inflorescence.*—Approximately 70.
*Color.*—Immature: Apex: 59B. Margin: 1D. Mature: Apex: 59A. Margin: 1D.
Phyllaries:
*Length.*—10 mm
*Width.*—1 mm. .
*Shape.*—Lanceolate.
*Apex.*—Acute.
*Margin.*—Entire.
*Number per inflorescence.*—45.
*Arrangement.*—Overlapping.
*Texture.*—Pubescence present.
*Color.*—Upper surface: 138A with stripes of 138B. Lower surface: 138B.
Peduncle:
*Length.*—Approximately 6–7 cm.
*Diameter.*—2 mm.
*Color.*—145A.
*Pubescence.*—Present.
*Strength.*—Strong.
Bud (described at 2 days before opening):
*Shape.*—Oval.
*Diameter.*—10 mm.
*Length.*—18 mm.
*Color.*—17A.
Disease resistance: Good resistance against Phytium and Phytophtora.
Fragrance: Faint; sweet.
Temperature tolerance: From 1° C. to 40° C.
Lasting quality: About 6 days with dry weather.
Drought tolerance: Good.

REPRODUCTIVE ORGANS

Androecium:
*Presence.*—On the disc.
*Number.*—Many.
*Filament length.*—3 mm.
*Anthers.*—Shape: Oval. Length: 1 mm. Color: 59A.
*Pollen.*—Color: 29A. Amount: Little.
Gynoecium:
*Presence.*—On the ray florets and some in the disc.
*Pistils.*—Number: Approximately 40. Length: Approximately 3 mm. Style: Length: 2 mm. Color: 155C. Stigma: Shape: Two-parted. Color: N89A.
Seeds:
*Description.*—Irregular production.
*Color.*—161C.
*Length.*—2 mm.
*Width.*—1 mm.
*Number.*—5 to 6.

I claim:

1. A new and distinct variety of *Osteospermum* plant substantially as shown and described.

* * * * *